US00PP21411P2

(12) United States Plant Patent
Ogden et al.

(10) Patent No.: US PP21,411 P2
(45) Date of Patent: Oct. 19, 2010

(54) ***SALVIA* PLANT NAMED 'ULTRA VIOLET'**

(50) Latin Name: *Salvia×hybrida*
Varietal Denomination: Ultra Violet

(76) Inventors: Alan Scott Ogden, 2455 Stonecrest Dr., Fort Collins, CO (US) 80521; Lauren S. Ogden, 2455 Stonecrest Dr., Fort Collins, CO (US) 80521

( * ) Notice: Subject to any disclaimer, the term of this patent is extended or adjusted under 35 U.S.C. 154(b) by 56 days.

(21) Appl. No.: 12/315,144

(22) Filed: Nov. 26, 2008

(51) Int. Cl.
*A01H 5/00* (2006.01)

(52) U.S. Cl. ..... Plt./475

(58) Field of Classification Search ..... Plt./475
See application file for complete search history.

(56) References Cited

U.S. PATENT DOCUMENTS

2009/0328267 P1 * 12/2009 Bernabe ..... Plt./475

* cited by examiner

*Primary Examiner*—Wendy C. Haas

(57) ABSTRACT

A new and distinct cultivar of *Salvia* named 'ULTRA VIOLET' that is characterized by compact habit, many flowers, small green leaves, and deep-purple flowers with dark calyces. In combination these traits set 'ULTRA VIOLET' apart from all other existing varieties of *Salvia* known to the inventors.

2 Drawing Sheets

Genus: *Salvia.*
Species: *xhybrida.*
Denomination: 'ULTRA VIOLET'.

BACKGROUND OF THE INVENTION

The present invention relates to a new and distinct cultivar of *Salvia* grown as an ornamental plant for garden and landscape. The new invention from the family Lamiaceae is known botanically as *Salvia xhybrida* and will be referred to hereinafter by the cultivar name 'ULTRA VIOLET'.

'ULTRA VIOLET' was discovered as a chance seedling resulting from uncontrolled open cross-pollination between an individual *Salvia lycioides* (species, unpatented) as female parent and an individual *Salvia greggii* 'Pink Preference' (unpatented) as male parent. *Salvia lycioides* seed was collected in 2003 and sown by the inventors to produce a commercial crop. The inventors discovered 'ULTRA VIOLET' in and amongst the resulting commercial crop of *Salvia lycioides* at the inventors' nursery in Fort Collins, Colo. The inventors selected 'ULTRA VIOLET' in 2003 based on the criteria of flower color and flower quantity.

Distinguishing characteristics of the new variety named 'ULTRA VIOLET' include compact habit, small aromatic green leaves, small overall shrub size, many flowers, dark calyces and deep-purple flower color. The deep-purple flowers combine with the dark calyces to create a fluorescent quality to the flower appearance. The stems and foliage of 'ULTRA VIOLET' exhibit aromatic properties. Shrub dimensions in the first year are 30 cm. in height and 30 cm. in width. Mature dimensions range from 60 cm to 90 cm. in height and from 60 cm to 90 cm. in width. Cultural requirements include full sun, well draining soil, and minimal water. 'ULTRA VIOLET' is generally hardy to USDA Zone 6, but established plants appear to exhibit adaptability to extreme cold.

'ULTRA VIOLET' is distinguishable from the parents by flower color, foliage size, and overall shrub size. The overall shrub and leaf of 'ULTRA VIOLET' are intermediate in size between those of the parents. 'ULTRA VIOLET' is distinguishable from the parents by deep-purple flower color. *Salvia lycioides* exhibits blue flower color and *Salvia greggii* 'Pink Preference' exhibits reddish-pink flower color. The closest comparison plant is *Salvia greggii* 'Pink Preference'. 'ULTRA VIOLET' is distinguishable from the comparison plant by flower color, flower quantity, leaf size, and overall shrub size.

The first asexual propagation of 'ULTRA VIOLET' took place in 2004 at the inventors' nursery in Fort Collins, Colo. The method used was vegetative cuttings. Since that time under careful observation 'ULTRA VIOLET' has been determined stable, uniform, and true to type in subsequent generations of asexual propagation.

SUMMARY OF THE INVENTION

The following traits have been repeatedly observed and represent the distinguishing characteristics of the new *Salvia* cultivar named 'ULTRA VIOLET'.

These traits in combination set 'ULTRA VIOLET' apart from all other existing varieties of *Salvia* known to the inventors. 'ULTRA VIOLET' has not been tested under all possible conditions and phenotypic differences may be observed with variations in environmental, climatic, and cultural conditions without however any variance in genotype.

1. 'ULTRA VIOLET' bears a large number of deep-purple flowers that exhibit dark calyces, creating a fluorescent quality to the flower appearance.
2. 'ULTRA VIOLET' exhibits compact habit.
3. 'ULTRA VIOLET' exhibits small green leaves, and small overall shrub size.
4. 'ULTRA VIOLET' exhibits aromatic properties.
5. 'ULTRA VIOLET' reaches a height that ranges from 60 cm-90 cm. and a width that ranges from 60cm-90 cm. at maturity.
6. 'ULTRA VIOLET' is hardy to USDA Zone 6.

BRIEF DESCRIPTION OF THE DRAWINGS

The accompanying color drawing illustrates the overall appearance of 'ULTRA VIOLET' showing the color as true as is reasonably possible to obtain in color reproductions of this type. Color in the drawings may differ from color values cited in the detailed botanical description, which accurately describe the actual color of 'ULTRA VIOLET'.

The drawing labeled

The drawing labeled

Figure 1:
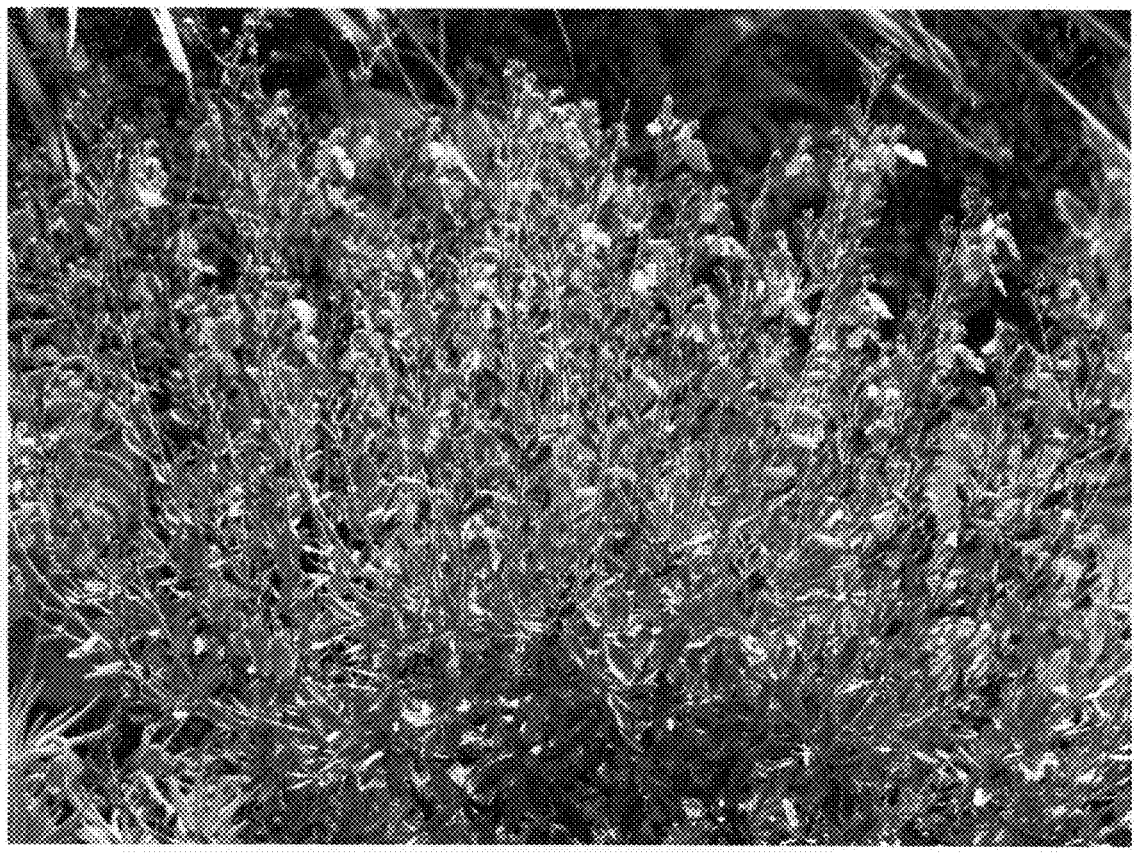
FIG. 1 illustrates a two year old plant of 'ULTRA VIOLET' growing out-of-doors in a garden setting.
Figure 2:
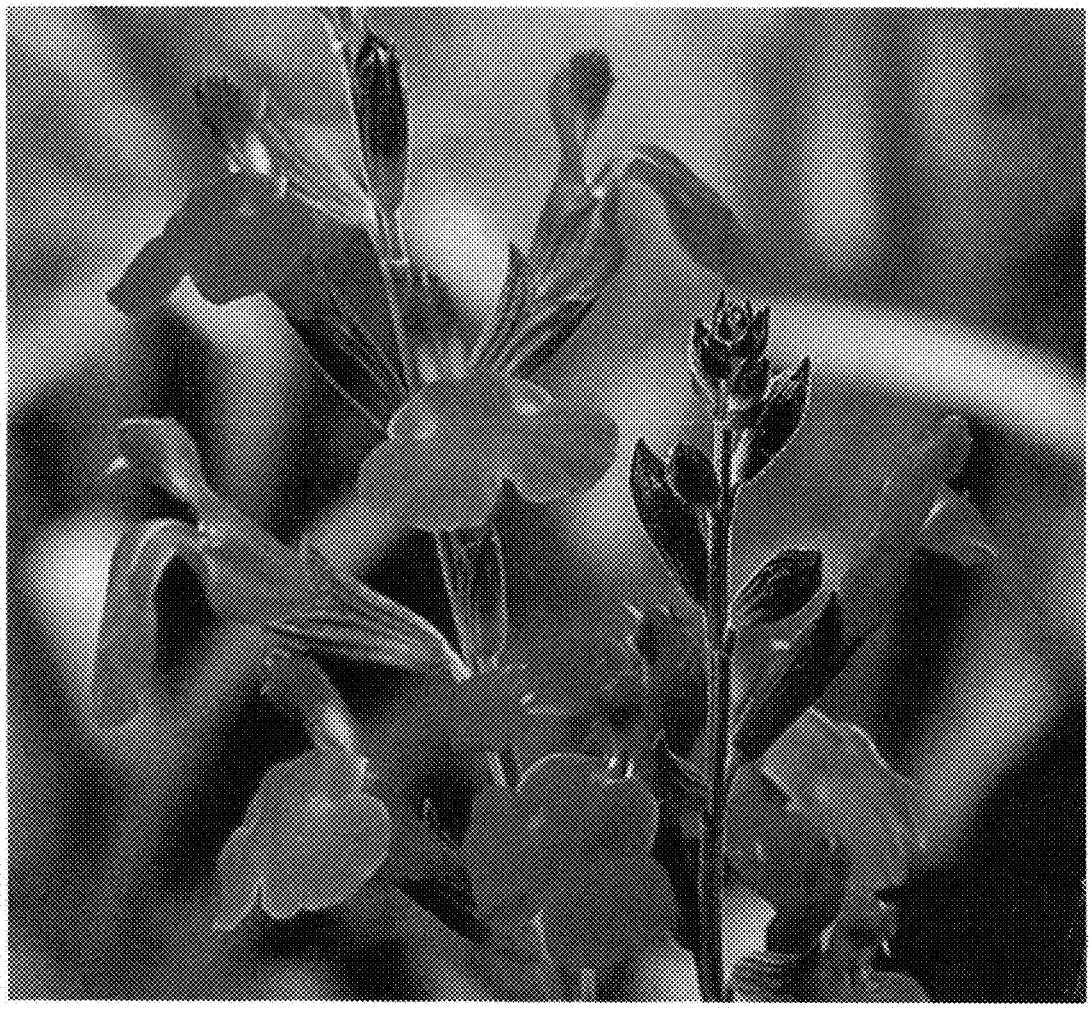
FIG. 2 illustrates a close-up view of an inflorescence of a one year old plant of 'ULTRA VIOLET' showing the deep purple colored flowers and the deeper purple colored buds and the dark calyx.

Both drawings were made using conventional techniques and although flower and foliage color may appear different from actual color due to light reflectance, the drawing is as accurate as possible by conventional photography.

DETAILED BOTANICAL DESCRIPTION

The following is a detailed botanical description of the new *Salvia* cultivar named 'ULTRA VIOLET' known commonly as sage. Observations, measurements, values and comparisons were collected in Arroyo Grande, Calif., from 9-month-old plants grown out-of-doors in 2-liter containers. Color determinations are made in accordance with The 2001 Royal Horticultural Society Colour Chart from London, England, except where general color terms of ordinary dictionary significance are used. The growing requirements of the new *Salvia* variety named 'ULTRA VIOLET' are similar to the species.

Botanical classification: *Salvia xhybrida* 'ULTRA VIOLET'.
Family: Lamiaceae.
Genus: *Salvia.*
Species: *xhybrida.*
Denomination: 'ULTRA VIOLET'.
Common name: Sage.
Habit: Compact.
Commercial category: Ornamental.
Use: For garden and landscape.
Suggested commercial container size: 1-liter container.
Parentage: *Salvia xhybrida* 'ULTRA VIOLET' is a chance seeding resulting from open cross-pollination between the following parents:
- *Female parent.*—An individual *Salvia lycioides.*
- *Male parent.*—An individual *Salvia greggii* 'Pink Preference' (unpatented).

Propagation method: Vegetative cuttings.
Rooting system: Fine and fibrous.
Vigor (range): Moderate to vigorous.
Crop time (range): 6-9 months to produce a 1-liter container from stem cuttings.
Temperature (range): The recommended air temperature is 20-21° Centigrade.
Plant dimensions (first year): 30 cm. in height and 30 cm. in width.
Plant dimensions (range at maturity): 60-90 cm. in height and 60-90 cm. in width.
Cultural requirements: Grow in full sun, well draining soil, with minimal water.
Pest or disease resistance: None known to the inventors.
Pest or disease susceptibility: None known to the inventors.
Hardiness: USDA Zone 6.
Special considerations: Established plants are adaptable to extreme cold.

Stem:
- *Shape.*—Quadrangular.
- *Surface.*—Pubescent.
- *Color.*—138B.
- *Length* (*average*).—30 cm.
- *Width* (*average*).—0.20 cm.
- *Internode* (*average*).—1.50 cm.
- *Fragrance.*—Aromatic.

Foliage:
- *Type.*—Evergreen.
- *Arrangement.*—Opposite.
- *Division.*—Simple.
- *Margin.*—Entire.
- *Surface* (*abaxial and adaxial*).—Puberulent.
- *Shape* (*range*).—Lanceolate to oblanceolate.
- *Length* (*average*).—2 cm.
- *Width* (*range*).—0.50-1 cm.
- *Abaxial surface color.*—137D.
- *Adaxial surface color.*—137C.
- *Apex* (*range*).—Acute to rounded.
- *Base* (*range*).—Attenuate to rounded.
- *Venation pattern.*—Pinnate.
- *Vein color* (*abaxial and adaxial surfaces*).—137C.
- *Attachment.*—Petiolate.
- *Petiole shape.*—Quadrangular.
- *Petiole surface.*—Puberulent.
- *Petiole color.*—N138C.
- *Petiole dimensions.*—3 mm. in length and <1 mm. in width.
- *Fragrance.*—Aromatic.

Inflorescence:
- *Inflorescence.*—Raceme.
- *Inflorescence dimensions* (*range*).—5-10 cm. in length and 3-4 cm. in width.
- *Blooming season* (*range*).—Summer to fall.
- *Flower quantity* (*average*).—200 flowers or more per 2-liter container plant.
- *Persistent or self-cleaning.*—Self-cleaning.
- *Aspect.*—Facing upward and outward.
- *Bud shape.*—Ovoid.
- *Bud dimensions.*—1 cm. in length and 0.25 cm. in width.
- *Bud color.*—N92A.
- *Bud surface.*—Pubescent.
- *Bud apex.*—Rounded.
- *Corolla shape.*—Bilabiate.
- *Corolla color.*—83A, N81A, 77A and N155A are all individually present.
- *Corolla dimensions.*—2.50 cm. in depth and 1.50 cm. in diameter.
- *Corolla tube shape.*—Tubular and gibbous.
- *Corolla tube color.*—77A.
- *Corolla tube dimensions.*—12 mm. in depth and 4 mm. in diameter.
- *Corolla tube surface* (*ventral and dorsal*).—Pubescent.
- *Corolla lip.*—2 in number. Upper lip shape (range): Falcate to helmet. Upper lip aspect: Erect. Upper lip dimensions: 9 mm. in length and 3 mm. in width. Upper lip color: 83A, N81A and N155A are all individually present. Upper lip margin: Villous. Villi color: 83A. Lower lip shape: 4-Lobed. Lower lip aspect: Reflexed. Lower lip dimensions: 1 cm. in length and 1.50 cm. in width. Lower lip color: 83A and N81A. Lobes fused or unfused: Fused. Lobe margin: Entire. Lobe surface (abaxial and adaxial): Stipitate glandular.

*Calyx shape.*—Tubular.
*Calyx dimensions.*—7 mm. in length and 3 mm. in width.
*Calyx surface.*—Pubescent.
*Calyx color.*—N92A and N144A.
*Sepal.*—3 in number.
*Fused or unfused.*—Fused.
*Sepal apex.*—Acute.
*Sepal color.*—N92A and N144A.
*Pedicel color.*—N92A and N144A.
*Pedicel dimensions.*—3 mm. in length and <1 mm. in width.
*Peduncle color.*—N92A and N144A.
*Peduncle dimensions* (*average*).—5-10 cm. in length and 0.20 cm. in width.
*Peduncle shape.*—Quadrangular.
*Peduncle surface.*—Pubescent.
*Flower fragrance.*—None observed.
*Lastingness of flower* (*range*).—3-5 days.

Reproductive organs:

*Stamen quantity.*—2 in number.
*Stamen length.*—6 mm.
*Stamen color.*—N155A.
*Anther color.*—17A.
*Anther length.*—2 mm.
*Pollen amount.*—Moderate.
*Pollen color.*—17A.
*Pistil quantity.*—1 in number.
*Pistil length.*—13 mm.
*Pistil color.*—N155A.
*Stigma dimensions.*—2 mm. in height and 3 mm. in width.
*Stigma shape.*—Forked.
*Stigma color.*—N79A.
*Ovary position.*—Superior.
*Ovary shape.*—Elongated ovoid.
*Ovary dimensions.*—3 mm. in height and 2 mm. in diameter.
*Ovary color.*—N144A.

Claim:

1. A new and distinct cultivar of *Salvia* plant named 'ULTRA VIOLET' as described and illustrated herein.

* * * * *